United States Patent
Gu et al.

(10) Patent No.: US 7,323,607 B2
(45) Date of Patent: Jan. 29, 2008

(54) PROCESS FOR PREPARATION OF (+)-P-MENTHA-2,8-DIENE-1-OL

(75) Inventors: Hong Gu, St. Louis, MO (US); J. Kendall Killgore, St. Louis, MO (US); John R. Duchek, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 323 days.

(21) Appl. No.: 10/549,976

(22) PCT Filed: Apr. 14, 2004

(86) PCT No.: PCT/US2004/011509

§ 371 (c)(1),
(2), (4) Date: Sep. 20, 2005

(87) PCT Pub. No.: WO2004/096740

PCT Pub. Date: Nov. 11, 2004

(65) Prior Publication Data

US 2006/0084828 A1    Apr. 20, 2006

Related U.S. Application Data

(60) Provisional application No. 60/465,046, filed on Apr. 24, 2003.

(51) Int. Cl.
   *C07C 35/18* (2006.01)
(52) U.S. Cl. .................. 568/825; 568/822; 568/823

(58) Field of Classification Search ................ 568/825, 568/822, 823
See application file for complete search history.

(56) References Cited

U.S. PATENT DOCUMENTS

| | | | |
|---|---|---|---|
| 3,538,164 A | 11/1970 | Leffingwell et al. |
| 3,734,930 A | 5/1973 | Razdan et al. |
| 3,814,733 A | 6/1974 | Bledsoe, Jr. et al. |
| 4,025,516 A | 5/1977 | Razdan et al. |
| 4,179,517 A | 12/1979 | Mechoulam et al. |
| 4,296,257 A | 10/1981 | Cardenas et al. |
| 4,433,183 A | 2/1984 | Fehr et al. |
| 5,777,137 A | 7/1998 | Hudkicky et al. |
| 6,262,278 B1 | 7/2001 | Jacobsen et al. |

OTHER PUBLICATIONS

J. G. Smith, Synthetically Useful Reactions of Epoxides, Synthesis 1984, pp. 629-656.
Arthur C. Cope, Olefins From Amines: The Hofmann Elimination Reaction and Amine Oxice Pyrolysis, Organic Reaction, vol. II, 1960, pp. 317-492.

*Primary Examiner*—Elvis O. Price
(74) *Attorney, Agent, or Firm*—Sarah Pfeifer Vaz; Blackwell Sanders LLP

(57) ABSTRACT

A process for preparing (+)-p-mentha-2,8-diene-1-ol comprising reacting (+)-limonene oxide with at least one amine in the presence of at least one Lewis acid to form amine adduct intermediates. The amine adduct is then oxidized to form an N-oxide that is pyrolized to form (+)-p-mentha-2,8-diene-1-ol.

22 Claims, No Drawings

PROCESS FOR PREPARATION OF (+)-P-MENTHA-2,8-DIENE-1-OL

CROSS REFERENCE TO RELATED APPLICATIONS

This application is a national stage application of PCT/US2004/011509, filed Apr. 14, 2004, which claims the benefit of U.S. Provisional Application No. 60/465,046, filed Apr. 24, 2003.

FIELD OF THE INVENTION

The present relation relates to a process for regio- and stereoselective opening of an epoxide ring, and more particularly to the regio- and stereoselective conversion of (+)-limonene oxide to (+)-p-mentha-2,8-diene-1-ol.

BACKGROUND OF THE INVENTION

Epoxides, also known as oxiranes, are useful intermediates in synthesizing active pharmaceutical ingredients and drugs. The inherent polarity and strain of the three-membered ring makes them susceptible to reaction with a large number of reagents. Of particular interest is the stereoselective nucleophilic attack of the epoxide ring to form 1,2-di-substituted products.

$\Delta^9$-Tetrahydrocannabinol (THC) is one of the biologically active components of cannabis. Pharmaceutical interest in THC has increased due to FDA approval for several therapeutic applications. Many of the known processes for the preparation of THC utilize (+)-p-mentha-2,8-diene-1-ol or an analog thereof as an intermediate. The (+)-p-mentha-2,8-diene-1-ol or an analog can be prepared from limonene through a synthesis that includes opening an epoxy ring. Conventional methods for converting limonene into (+)-p-mentha-2,8-diene-1-ol include oxidizing limonene with singlet oxygen and conversion using an enzymatic reaction.

Previous methods to synthesize (+)-p-mentha-2,8-diene-1-ol present certain drawbacks when attempts are made to produce on a commercial scale. Many of these methods result in the formation of significant isomeric mixtures of intermediates and the final product, requiring chiral resolution. Previous methods are therefore too costly and/or complicated to scale up to commercial scale. To this date there is no known commercial process for the production of (+)-p-mentha-2,8-diene-1-ol or its' analogs.

It is therefore desirable to provide a regio- and stereoselective process for opening an epoxide ring, thereby providing a regio- and stereoselective process for preparing (+)-p-mentha-2,8-diene-1-ol.

SUMMARY OF THE INVENTION

An aspect of the present invention is to provide a process for the regio- and stereoselective opening of an epoxide ring, the process comprising reacting a compound having the epoxide ring with at least one amine in the presence of at least one Lewis acid.

Another aspect of the present invention is to provide a process for preparing (+)-p-mentha-2,8-diene-1-ol and analogs thereof. In a preferred embodiment the process comprises reacting (+)-limonene oxide with an amine in the presence of a Lewis acid to form amine adduct intermediates. The desired amine adduct intermediate is formed at a ratio of greater than 20:1 over other reaction products. The desired amine adduct is then oxidized to form an N-oxide that is pyrolized to form (+)-p-mentha-2,8-diene-1-ol. In an alternative embodiment the amine adduct is converted to an acid salt and then base hydrolyzed to form (+)-p-mentha-2,8-diene-1-ol.

These are merely two illustrative aspects of the present invention and should not be deemed an all-inclusive listing of the innumerable aspects associated with the present invention. These and other aspects will become apparent to those skilled in the art in light of the following disclosure.

DETAILED DESCRIPTION OF THE INVENTION

There is provided a process for the regio- and stereoselective opening of an epoxide ring, where one carbon of the epoxide ring is more substituted. A compound having such an epoxide ring is reacted with an amine in the presence of a Lewis acid. The chemistry for the reaction of the epoxide ring with secondary amines is known in the art. However, by introducing a Lewis acid catalyst to chelate or complex with the oxygen atom of the epoxide, the partial charge on the two carbon atoms of the epoxide ring is changed. Experimental results suggest that the less substituted carbon is more prone to nucleophilic attack. This allows for the regio- and stereoselective opening of the epoxide ring.

This process can be used to prepare (+)-p-mentha-2,8-diene-1-ol and analogs thereof, as follows:

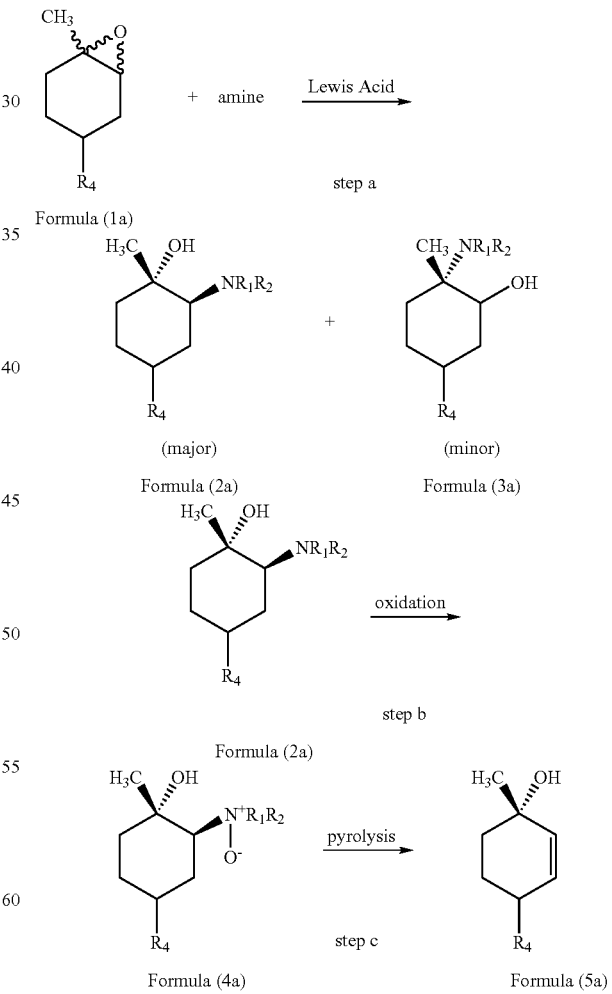

wherein $R_1$, $R_2$ and $R_3$ are H, alkyl or aryl groups;
wherein $R_4$ is an alkyl, alkenyl or alcohol.

This process is described in more detail in the following example of a process for the regio-and stereoselective preparation of (+)-p-mentha-2,8-diene-1-ol as follows:

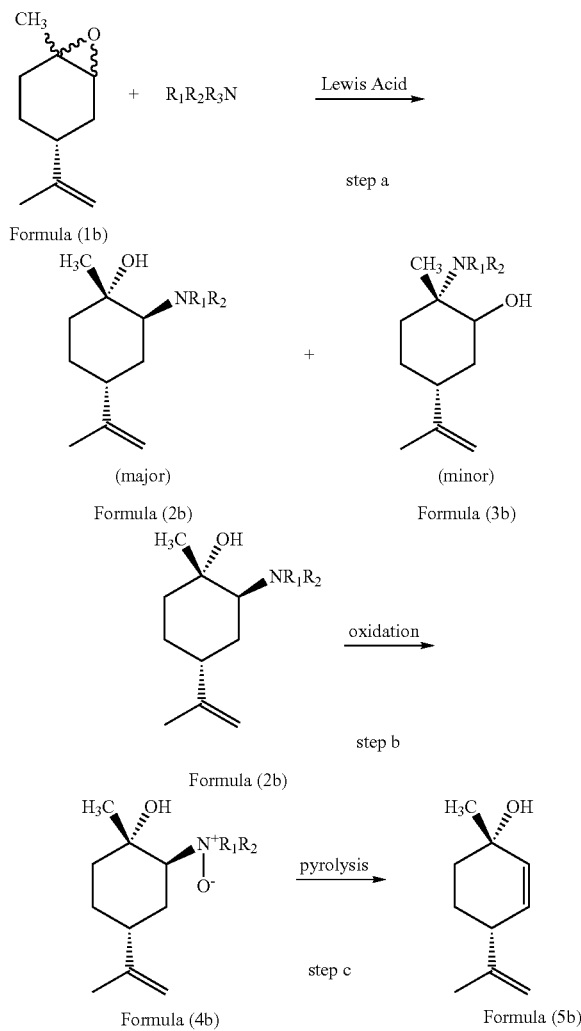

wherein $R_1$, $R_2$ and $R_3$ are H, alkyl or aryl groups;

Reaction step (a) comprises reacting a mixture of cis and trans isomers of (+)-limonene oxide (Formula (1b)) with at least one amine in the presence of at least one Lewis acid. The amine may be primary, wherein $R_2$ and $R_3$ are H; secondary, wherein $R_3$ is H; or tertiary. The choice of $R_1$ in the primary amine, $R_1$ and $R_2$ in the secondary amine and $R_1$, $R_2$ and $R_3$ in the tertiary amine are limited only in that $R_1$, $R_2$ and $R_3$ must not interfere with the reaction, either by chemical reaction or sterically. For practical reasons suitable amines include, but are not limited to, amines wherein $R_1$, $R_2$ and $R_3$ are lower alkyl radicals having from about 1 to about 6 carbons, or aryl groups.

The Lewis acid may be any compound containing an element that is two electrons short of having a complete valence shell, as is well known in the art. Suitable Lewis acids include but are not limited to non-protic acids including metals, primarily halides, alkyls, and ether complexes thereof. Suitable alkyl metal halides include MRX wherein R is an alkyl, preferably having 1 to 6 carbons. M is a metal, including but not limited to Group II metals, and X is a halide. Suitable ether complexes include those of the formula MOR, wherein M is a metal and R is an alkyl, preferably having 1 to 6 carbons. While the metal is typically selected from Group I alkali metals, any suitable metal may be utilized. In one embodiment of the present invention, M is selected from Li, K and Na, and R is selected from methyl, ethyl, propyl or butyl.

The reaction products of step (a) are the amine adducts Formula (2b) and Formula (3b). Step (a) leads to a significant improvement of the regio- and stereoselectivity of the reaction of (+)-limonene oxide with the primary or secondary amine. Only one major product, the desired Formula (2b), is produced. Formula (2b) is formed at a ratio of greater than 20:1 over Formula (3b). The Lewis acid also allows the reaction to be carried out at lower temperatures than previously, typically 30° C. to 80° C., with about 500° C. being preferred in an embodiment utilizing LiOAc as the Lewis acid.

Another advantage of the present invention is that the (+)-trans-limonene oxide does not react and can be easily recovered by well known methods, thereby providing a means for diastereomeric separation of the two (+)-limonene oxide isomers. The Formula (2b) amine adduct intermediate is also easily purified by making and acid salt. Suitable acids include but are not limited to HCl salt using concentrated hydrochloric acid (37%).

In step (b), the amine adduct of Formula (2b) is oxidized to form the N-oxide of Formula (4b). In a preferred embodiment the amine adduct Formula (2b) is oxidized with a peracid, for example about 30% to about 50% hydrogen peroxide ($H_2O_2$) in the presence of at least one alcohol. Suitable alcohols include but are not limited to alkyl alcohols having, for practical reasons, from about 1 to about 6 carbons, including but not limited to methanol, ethanol, propanol, isopropanol, butanol, t-butanol, and branched, unbranched and cyclic pentanol and hexanol. This reaction is also accomplished at a relatively lower temperature, about 50° C. when the alcohol utilized is ethanol.

In step (c), the N-oxide intermediate Formula (4b) is pyrolized to produce (+)-p-mentha-2,8-diene-1-ol. This pyrolysis reaction to eliminate the tertiary amine oxide is known as a Cope elimination. In a preferred embodiment the pyrolysis takes place in a solvent system including toluene at a temperature of at least about 110° C., or at any temperature at which the pyrolysis reaction will occur given the experimental conditions. In an alternative embodiment, the pyrolysis takes place in toluene in the presence of at least one particulate matter such as zeolites or silica gels. In a preferred embodiment the particulate matter is $SiO_2$ or molecular sieves.

The overall yield of the conversion of (+)-limonene oxide to (+)-p-mentha-2,8-diene-1-ol of the present invention is typically about 50%.

An alternative embodiment for the conversion of the amine adduct to (+)-p-mentha-2,8-diene-1-ol or an analog thereof is illustrated below:

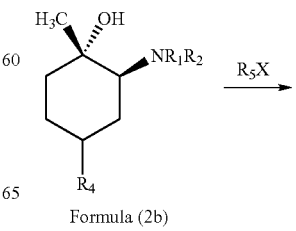

Formula (2b)

-continued

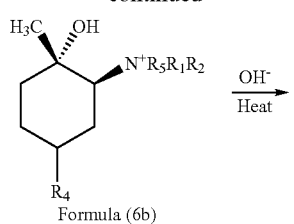

Formula (6b)

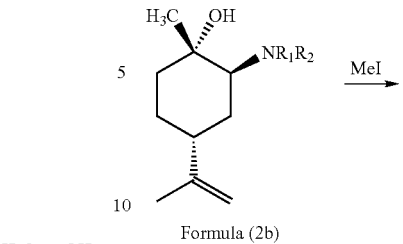

Formula (2b)

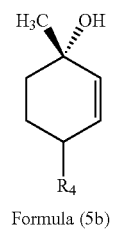

Formula (5b)

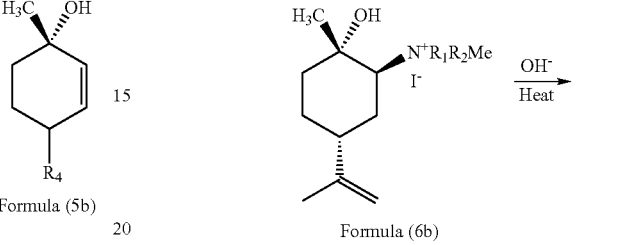

Formula (6b)

wherein $R_1$ and $R_2$ are H, alkyl or aryl;
wherein R5 is an H, aryl or alkyl;
wherein $R_4$ is an alkyl, alkenyl or alcohol; and
wherein X is a halide.

This alternative process is described in more detail in the following example for the preparation of (+)-p-mentha-2,8-diene-1-ol as follows:

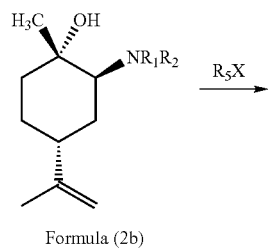

Formula (2b)

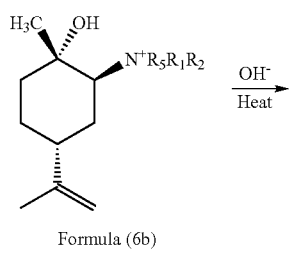

Formula (6b)

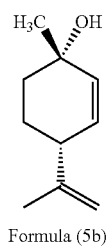

Formula (5b)

The amine adduct of Formula (2b) reacts with the $R_5X$ to form the quaternary salt of Formula (6b) that is then heated under basic condition to form (+)-p-mentha-2,8-diene-1-ol of Formula (5b). In a one suitable embodiment, MeI is used, as illustrated below.

The amine adduct of Formula (2b) is converted to the quaternary salt of Formula (6b), and then base hydrolyzed under heat to form (+)-p-mentha-2,8-diene-1-ol of Formula (5b).

The following examples are offered to illustrate the process of the present invention, and are not intended to limit or define the present invention in any manner.

EXAMPLES

Example 1

PREPARATION OF (1S,2S,4R)-2-(N-MORPHOLI-NYL)-1-METHYL-4-(1-METHYLETHENYL)-CYCLOHEXANOL 40.00 g (0.26 mol) of (+)-limonene oxide was dissolved into 90 ml of ethanol and placed into a 250 ml 3 neck round bottom flask. Anhydrous lithium acetate (LiOAc) 28 g (0.42 mol) was added in portions over 3 minutes to the above mixture and stirred at 50° C. for about 30 minutes. 22 g (0.26 mol) of morpholine dissolved in 30 ml of EtOH to give a clear solution was added dropwise by an addition funnel into the reaction mixture at a rate slow enough to maintain the temperature below 60° C. The reaction mixture was stirred at 50° C. for about 16 hours.

Upon completion of the reaction, the ethanol was distilled off from the reaction mixture under vacuum to give a light yellow oil. The oil was then re-dissolved into 200 ml of chloroform, and the resulting solution was washed with 100 ml of deionized water twice and 100 ml of brine once, and finally dried with anhydrous $MgSO_4$. The solid was filtered out and the solvent removed under vacuum to give a light yellow oil. The reaction product was analyzed by HPLC and compared to an authentic sample. The results indicated that the reaction product contained the major product 2b and a minor amount of 3b. The major product 2b (1S,2S,4R)-2-N-morpholinyl)-1-methyl-4-(1methylethenyl)-cyclohexanol was further purified by re-crystallization in isopropanol. $^1$H NMR $\delta_H$ (300 MHz, CDCl$_3$): 1.15-1.32 (4H,m), 1.52 (3H, m), 1.73 (3H,s), 1.75 (3H,s), 2.05 (1H,s), 2.10 (1H,d), 2.51 (3H,m), 2.75 (2H,m), 3.7 (4H,m), 4.72 (1H,m), 4.9 (2H,dd). $^{13}$C NMR $\delta_C$ (300 MHz, CHCl$_3$): 14.19, 20.90, 22.34, 25.12, 26.24, 35.71, 38.96, 45.37, 52.01, 60.24, 67.45, 72.68, 110.97, 145.44.

Example 2

PREPARATION OF (1S,2S,4R)-2-(N-MORPHOLINYL)-1-METHYL-4-(1-METHYLETHENYL)-CYCLOHEXANOL (1S,2S,4R)-2-(N-morpholinyl)-1-methyl-4-(1-methylethenyl)-cyclohexene was synthesized as in Example 1, substituting lithium bromide in place of the lithium acetate in the reaction. A similar product mixture of Formula 2b and 3b was seen, with the ratio of 2b to 3b being greater than 20:1. The product was further purified and isolated by recrystallization in isopropanol.

Example 3

PREPARATION OF (1S,2S,4R)-2-(N-MORPHOLINYL)-1-METHYL-4-(1-METHYLETHENYL)-CYCLOHEXANOL (1S,2S,4R)-2-N-morpholinyl)-1-methyl-4-(1methylethenyl)-cyclohexanol was synthesized as in Example 1, substituting lithium chloride in place of the lithium acetate in the reaction. A similar product mixture of Formula 2b and 3b was seen, with the ratio of 2b to 3b being greater than 20:1. The product was further purified and isolated by recrystallization in isopropanol.

Example 4

PREPARATION OF (1S,2S,4R)-2-(N-MORPHOLINYL)-1-METHYL-4-(1-METHYLETHENYL)-CYCLOHEXANOL (1S,2S,4R)-2-N-morpholinyl)-1-methyl-4-(1methylethenyl)-cyclohexanol was synthesized as in Example 1, substituting aluminum oxide in place of the lithium acetate in the reaction. A similar product mixture of Formula 2b and 3b was seen, with the ratio of 2b to 3b being greater than 20:1. The product was further purified and isolated by recrystallization in isopropanol.

Example 5

PREPARATION OF (1S,2S,4R)-1-METHYL-4-(1-METHYLETHENYL)-2-(N-METHYLBENZYLAMINE)-CYCLOHEXANOL 10.00 g of (+)-limonene oxide was dissolved into 90 ml of ethanol and placed into a 250 ml 3 neck round bottom flask. 7 g of LiOAc hydrate was added to the above mixture and stirred at 50° C. for about 30 minutes. 20 g of benzylmethylamine was dissolved into 30 ml of EtOH and was added drop-wise into the reaction mixture over 10 minutes. The reaction mixture was continuously stirred at 50° C. for about 16 hours. The solvent was distilled off under vacuum to give light yellow oil. The oil was dissolved into 200 ml of CHCl$_3$ and the solution was washed with 100 ml of water twice, 100 ml of brine one and dried with anhydrous MgSO$_4$. The solid was removed by filtration and solvent was removed to give light yellow oil. HPLC analysis showed the major product is the 2b with some 3b. The (1S,2S,4R)-1-methyl-4-(1-methylethenyl)-2-(N-methylbenzylamine)-cyclohexanol was purified by recrystallization of its HCL salt in isopropanol. $^1$H NMR $\delta_H$ (300 MHz, CDCl$_3$): 1.53 (4H,m), 1.81 (3H,s), 1.92 (2H,m), 2.35 (1H,d), 2.90 (3H,s), 3.35 (3H,s), 3,70 (1H,d), 4.5 (2H,dd), 4.93 (2H,d), 7.3-7.7 (5H,m). $^{13}$C NMR $\delta_H$ (300 MHz, CHCl$_3$): 22.7, 24.5, 28.65, 39.3, 39.5, 49.8, 50.4, 73.9, 112.1, 128.3, 128.41, 129.8, 133.1, 133.4, 144.2, 165.0.

Example 6

PREPARATION OF (1S,2S,4R)-2-(N-PIPERIDINYL)-1-METHYL-4-(1-METHYLETHENYL)-CYCLOHEXANOL (1S,2S,4R)-2-(N-piperidinyl)-1-methyl-4-(1-methylethenyl)-cyclohexanol was synthesized as described in example 5, by utilizing piperidine as the amine. A similar product mixture of Formula 2b and 3was seen, with the ratio of 2b to 3b being greater than 20:1. The product, (1S,2S,4R)-2-N-piperidinyl)-1-methyl-4-(1methylethenyl)-cyclohexanol was further purified and isolated by recrystallization in isopropanol.

Example 7

PREPARATION OF (1S,2S,4R)-2-(N-PYRROLIDINYL)-1-METHYL-4-(1-METHYLETHENYL)-CYCLOHEXANOL (1S,2S,4R)-2-(N-pyrrolidinyl)-1-methyl-4-(1-methylethenyl)-cyclohexanol was synthesized as described in example 5, by utilizing pyrrolidine as the amine. A similar product mixture of Formula 2b and 3b was seen, with the ratio of 2b to 3b being greater than 20:1. The product, (1S,2S,4R)-2-N-pyrrolidinyl)-1-methyl-4-(1methylethenyl)-cyclohexanol was further purified and isolated by recrystallization in isopropanol.

Example 8

PREPARATION OF (1S,2S,4R)-2-(N-DIISOPROPYL)-1-METHYL-4-(1-METHYLETHENYL)-CYCLOHEXANOL (1S,2S,4R)-2-(N-diisopropylamine)-1-methyl-4-(1-methylethenyl)-cyclohexanol was synthesized as described in example 5, by utilizing diisopropylamine as the amine. A similar product mixture of Formula 2b and 3b was seen, with the ratio of 2b to 3b being greater than 20:1. The product, (1S,2S,4R)-2-(N-diisopropylamine)-1-methyl-4-(1methylethenyl)-cyclohexanol was further purified and isolated by recrystallization in isopropanol.

Example 9

PREPARATION OF (1S,2S,4R)-2-(N-MORPHOLINYL)-1-METHYL-4-(1-METHYLETHENYL)-CYCLOHEXANOL N-OXIDE

Dissolve 15 g of a Formula 2b from example 1 or 2 into 30 ml of EtOH, added 50% H$_2$O$_2$ into slowly over 30 minutes. The reaction mixture was stirred at 50° C. for about 4 hours, and the reaction progress was monitored by HPLC. Upon the complete conversion of the 2b to 4b as indicated by HPLC, catalytic amount of 5% Pd/C was added to the reaction mixture to decompose the unreacted hydrogen peroxide and the reaction mixture was continue stirred for about one hour. The reaction mixture was tested negative with the peroxides test strip. The catalyst was removed via filtration and solvent was evaporated under vacuum, a white solid was obtained. $^1$H NMR $\delta_H$ (300 MHz, CDCl$_3$): 1.15-1.32 (4H,m), 1.52 (3H,m), 1.73 (3H,s), 1.75 (3H,s), 2.05 (1H,s), 2.10 (1H,d), 2.51 (3H,m), 2.75 (2H,m), 3.7 (4H,m), 4.72 (1H,m), 4.9 (2H,dd). ). $^{13}$C NMR $\delta_C$ (300MHz, CHCl$_3$): 14.19, 20.90, 22.34, 25.12, 26.24, 35.71, 38.96, 45.37, 52.01, 60.24, 67.45, 72.68, 110.97, 145.44.

Example 10

PREPARATION OF (1R)-TRANS-1-METHYL-4-(1-METHYLETHENYL)-2-CYCLOHEXENE-1-OL 21 g (0.08 mol) of Formula 6b and 265 ml of toluene were charged in a reactor equipped with a Dean's trap and condenser. Silica oxide, 5 g, was added to the reaction mixture. The reaction mixture was heated to reflux for about 6 hours and followed by HPLC. Upon completion of the reaction the reaction mixture was filtered and the solvent evaporated under vacuum to give a dark colored oily residue. The product, (1R)-trans-1-methyl-4-(1-methylethenyl)-2-cyclohexene-1-ol, was recovered as a light yellow oil by fractional distillation under vacuum at 85° C. [α]D=63.9° C.(c=0.325 CHCl$_3$). $^1$H NMR $\delta_H$ (300 MHz, CDCl$_3$): 1.28 (3H,s), 1.40-1.66 (4H,m), 1.73 (3H,s), 1.80-1.86 (1H,m), 2.67 (1H,m), 4.73 (1H,s), 4.78 (1H,s) 5.67 (1H,d,J=11 Hz), 5.68 (1H,d,J=11 Hz). $^{13}$C NMR $\delta_C$ (300 MHz, CHCl$_3$): 20.81, 24.82, 29.35, 36.63, 43.42, 67.47, 110.55, 132.23, 133.92, 148.22.

Example 11

PREPARATION OF (1R)-TRANS-1-METHYL-4-(1-METHYLETHENYL)-2-CYCLOHEXENE-1-OL (1R)-trans-1-methyl-4-(1-methylethenyl)-2-cyclohexene-1-ol was synthesized as in example 10 utilizing molecular sieves 4A to replace the silica gel. HPLC indicated that a similar reaction product with less side products was obtained. The above compound was a colorless oil obtained by fractional distillation.

Example 12

PREPARATION OF (1R)-TRANS-1-METHYL-4-(1-METHYLETHENYL)-2-CYCLOHEXENE-1-OL (1R)-trans-1-methyl-4-(1-methylethenyl)-2-cyclohexene-1-ol was synthesized as in Example 10 utilizing Florosil to replace the silica gel. At the end of the reaction, HPLC indicated that similar dark reaction product mixture was obtained. The above compound was recovered as a colorless oil by fractional distillation.

From the foregoing description those skilled in the art will appreciate that a process for the regio- and stereoselective opening of an epoxy ring is provided. Further, an improved regio- and stereoselective process for preparation of (+)-p-mentha-2,8-diene-1-ol from (+)-limonene oxide is provided. The process of the present invention fewer steps than conventional methods and produces a high ratio of desired intermediates, thereby providing a process that can be easily and efficiently scaled up for commercial purposes.

Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

The invention claimed is:

1. A process for preparing a (+)-p-mentha-2,8-diene-1-ol analog, the process comprising:

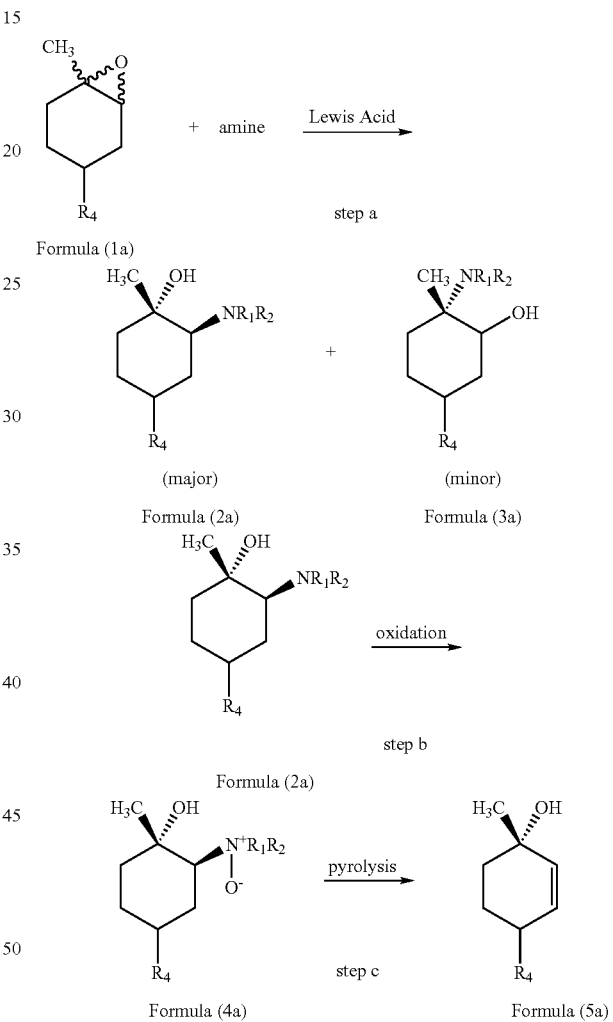

wherein R$_1$, R$_2$ and R$_3$ are H, alkyl or aryl;
wherein R$_4$ is an alkyl, alkenyl or alcohol;
wherein step (a) comprises reacting a (+)-limonene oxide analog having the Formula (1a) with at least one amine of the formula R$_1$R$_2$R$_3$N in the presence of at least one Lewis acid to form amine adducts having the Formula (2a) and Formula (3a);
wherein step (b) comprises oxidizing the amine adduct of Formula (2a) to form an N-oxide having Formula (4a); and
wherein step (c) comprises pyrolizing the N-oxide of Formula (4a) to form a (+)-p-mentha-2,8-diene-1-ol analog of Formula (5a).

2. The process according to claim 1 wherein the at least one Lewis acid is selected from the group consisting of alkyl metal halides and metal halide ethers.

3. A process for preparing (+)-p-mentha-2,8-diene-1-ol, the process comprising:

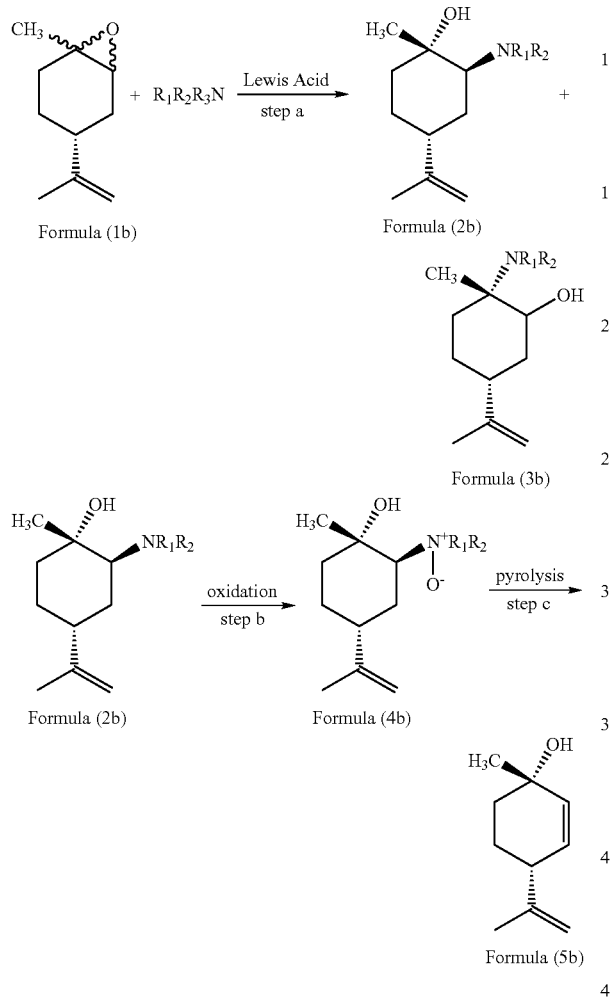

wherein $R_1$, $R_2$ and $R_3$ are H, alkyl or aryl groups;
wherein step (a) comprises reacting (+)-limonene oxide having the Formula (1b) with at least one amine of the formula $R_1R_2R_3N$ in the presence of at least one Lewis acid to form amine adducts having the Formula (2b) and Formula (3b);
wherein step (b) comprises oxidizing the amine adduct of Formula (2b) to form an N-oxide having Formula (4b); and
wherein step (c) comprises pyrolizing the N-oxide of Formula (4b) to form the (+)-p-mentha-2,8-diene-1-ol of Formula (5b).

4. The process according to claim 3 wherein the at least one amine is selected from the group consisting of primary amines wherein $R_1$ is an alkyl or aryl group and $R_2$ and $R_3$ are H; secondary amines wherein $R_1$ and $R_2$ are alkyl or aryl groups and $R_3$ is H; and tertiary amines wherein $R_1$, $R_2$ and $R_3$ are alkyl or aryl groups.

5. The process according to claim 3 wherein the at least one Lewis acid is selected from the group consisting of alkyl metal halides and metal a halide ethers.

6. The process according to claim 3 comprising oxidizing the amine adduct of Formula (2b) by reacting the amine adduct of Formula (2b) with at least one peracid to form the N-oxide of Formula (4b).

7. The process according to claim 3 comprising oxidizing the amine adduct of Formula (2b) by reacting the amine adduct of Formula (2b) with hydrogen peroxide in at least one alcohol to form the N-oxide of Formula (4b).

8. The process according to claim 3 comprising pyrolizing the N-oxide of Formula (4b) in a solvent system including toluene in the presence of an at least one particulate matter selected from the group consisting of zeolites and silica gels.

9. The process according to claim 3 further including recovering the amine adduct of Formula (2b) by converting the amine adduct to an acid salt of the amine adduct of Formula (2b) by reaction with concentrated acid.

10. A process for preparing a (+)-p-mentha-2,8-diene-1-ol analog, the process comprising:

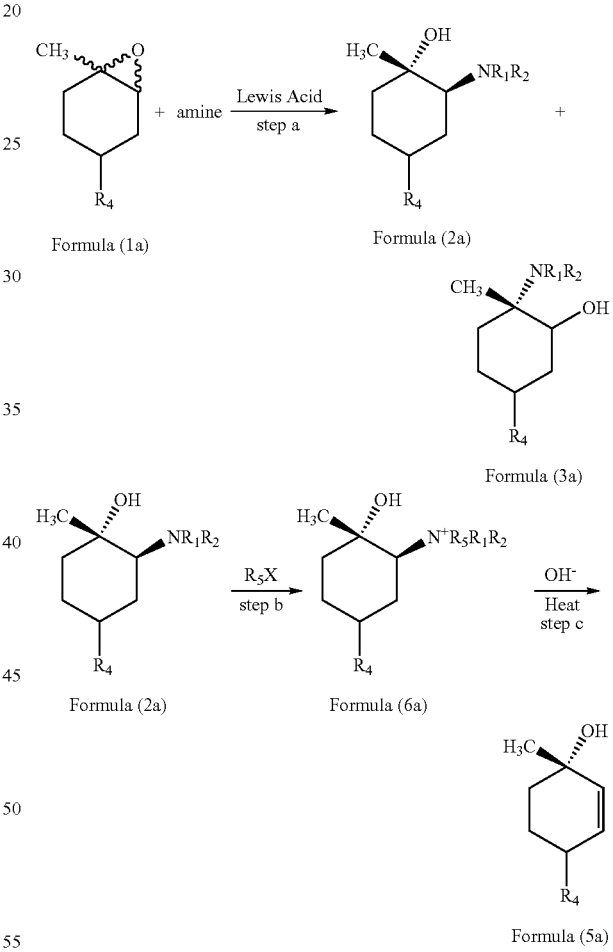

wherein $R_1$, $R_2$ and $R_3$ are H, alkyl or aryl groups;
wherein $R_4$ is an alkyl, alkenyl or alcohol;
wherein $R_5$ is an H, alkyl or aryl;
wherein X is a halide;
wherein step (a) comprises reacting a (+)-limonene oxide analog having the Formula (1a) with at least one amine of the formula $R_1R_2R_3N$ in the presence of at least one Lewis acid to form amine adducts having the Formula (2a) and Formula (3a);
wherein step (b) comprises converting the amine adduct of Formula (2a) to the acid salt of Formula (6a); and wherein step (c) comprises base hydrolyzing Formula (6a) to form the (+)-p-mentha-2,8-diene-1-ol analog of Formula (5a).

11. The process according to claim 10 wherein the at least one amine is selected from the group consisting of primary amines wherein $R_1$ is an alkyl or aryl group and $R_2$ and $R_3$ are H; secondary amines wherein $R_1$ and $R_2$ are alkyl or aryl groups and $R_3$ is H; and tertiary amines wherein $R_1$, $R_2$ and $R_3$ are alkyl or aryl groups.

12. The process according to claim 10 wherein the at least one Lewis acid is selected from the group consisting of alkyl metal halides and metal halide ethers.

13. The process according to claim 10 wherein $R_5X$ is methyl iodide.

14. A process for preparing (+)-p-mentha-2,8-diene-1-ol, the process comprising:

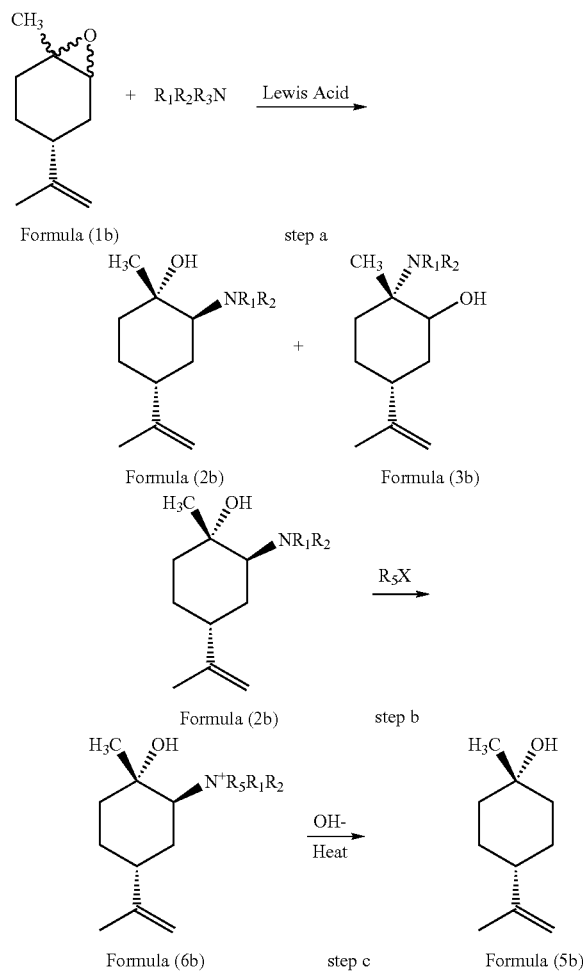

wherein $R_1$, $R_2$ and $R_3$ are H, alkyl or aryl groups;
wherein R5 is an H, alkyl or aryl;
wherein X is a halide;
wherein step (a) comprises reacting (+)-limonene oxide having the Formula (1b) with at least one amine of the formula $R_1R_2R_3N$ in the presence of at least one Lewis acid to form amine adducts having the Formula (2b) and Formula (3b);
wherein step (b) comprises converting the amine adduct of Formula (2b) to the acid salt of Formula (6b); and
wherein step (c) comprises base hydrolyzing Formula (6b) to form the (+)-p-mentha-2,8-diene-1-ol of Formula (5b).

15. The process according to claim 14 wherein the at least one amine is selected from the group consisting of primary amines wherein $R_1$ is an alkyl or aryl group and $R_2$ and $R_3$ are H; secondary amines wherein $R_1$ and $R_2$ are alkyl or aryl groups and $R_3$ is H; and tertiary amines wherein $R_1$, $R_2$ and $R_3$ are alkyl or aryl groups.

16. The process according to claim 14 wherein the at least one Lewis acid is selected from the group consisting of alkyl metal halides and metal halide ethers.

17. The process according to claim 14 wherein $R_5X$ is MeI.

18. A method for the diastereomeric separation of a mixture of (+)-cis-limonene oxide and (+)-trans-limonene, the method comprising:
reacting the mixture with an amine in the presence of a Lewis acid; and
recovering the (+)-cis-limonene oxide that does not react with the amine.

19. The process according to claim 1 wherein the Lewis acid is selected from the group consisting of lithium acetate, lithium bromide, lithium chloride, aluminum oxide and mixtures thereof.

20. The process according to claim 3 wherein the Lewis acid is selected from the group consisting of lithium acetate, lithium bromide, lithium chloride, aluminum oxide and mixtures thereof.

21. The process according to claim 10 wherein the Lewis acid is selected from the group consisting of lithium acetate, lithium bromide, lithium chloride, aluminum oxide and mixtures thereof.

22. The process according to claim 14 wherein the Lewis acid is selected from the group consisting of lithium acetate, lithium bromide, lithium chloride, aluminum oxide and mixtures thereof.

* * * * *